United States Patent [19]

Benkő et al.

[11] 4,424,351
[45] Jan. 3, 1984

[54] PYRIDO[3,4-E]-AS-TRIAZINES

[75] Inventors: Pál Benkó; Györgyi née Lax Kovànyi; Judit née Gergely Timár; Mária née Lakatos Sigmond; Lujza Petöcz; Péter Görög; Ibolya Kosóczky; Enikó née Kiszelly Szirt; Hristoné Toncsev, all of Budapest, Hungary

[73] Assignee: Egyt Gyogyszervegyeszeti Gyar, Budapest, Hungary

[21] Appl. No.: 123,807

[22] Filed: Feb. 22, 1980

[30] Foreign Application Priority Data

Feb. 23, 1979 [HU] Hungary .............. EE-2634

[51] Int. Cl.³ .................. A61K 31/53; C07D 471/04
[52] U.S. Cl. ........................... 542/439; 544/184; 424/249
[58] Field of Search ............ 544/184; 542/439; 424/249

[56]         References Cited
           U.S. PATENT DOCUMENTS
  3,597,427  8/1971  Lewis et al. .................. 544/184
           FOREIGN PATENT DOCUMENTS
  3006719  9/1980  Fed. Rep. of Germany .
           OTHER PUBLICATIONS
Armand et al., *J. Org. Chem.*, vol. 46, pp. 4754–4759 (1981).

*Primary Examiner*—John M. Ford
*Attorney, Agent, or Firm*—Young & Thompson

[57]           ABSTRACT

Acylated pyrido [3,4-e]-as-triazines of the formula (I),

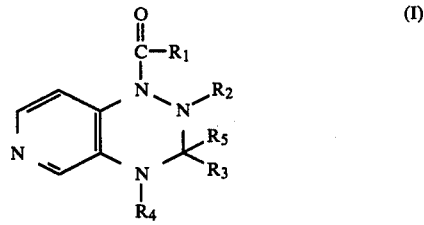

wherein $R_1$ stands for alkyl, alkoxy, haloalkyl, furyl, pyridyl, phenyl, phenyl-($C_{1-4}$alkyl) or phyenyl-($C_{2-4}$ alkenyl) optionally substituted. $R_2$ stands for hydrogen or a group of the formula $R_1$—CO—, $R_3$ stands for hydrogen, a phenyl group or a naphthy6l group optionally substituted, or a phenyl-($C_{1-4}$alkyl) group, pyridyl group or a $C_{1-20}$alkyl group, and $R_4$ stands for hydrogen or a group of the formula $R_1$—CO—, and $R_5$ forms together with $R_2$ or $R_4$ a valence bond, wherein $R_2$ or $R_4$ taking part in forming said valence bond may not have the above meaning, and pharmaceutically acceptable acid addition salts thereof, which are prepared by reacting a pyrido [3,4-e]-as-triazine of the formula (II) or an acid addition salt thereof

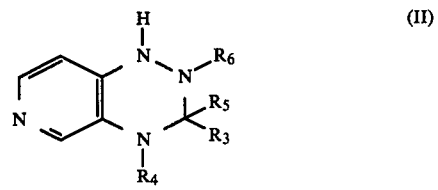

$R_6$ stands for hydrogen, and $R_5$ forms together with Rand $R_4$ a valence bond, with an acylating agent of the formula (III).

$$R_1\text{—CO—X} \qquad (III)$$

The compounds exert favourable effects on the central nervous system, and can be applied primarily as analgesic and antiphlogistic agents.

8 Claims, No Drawings

PYRIDO[3,4-E]-AS-TRIAZINES

The invention relates to new pyrido[3,4-e]-as-triazine derivatives and pharmaceutical compositions containing the same, furthermore to a process for the preparation thereof.

The new pyrido[3,4-e]-as-triazine derivatives of the invention correspond to the general formula (I),

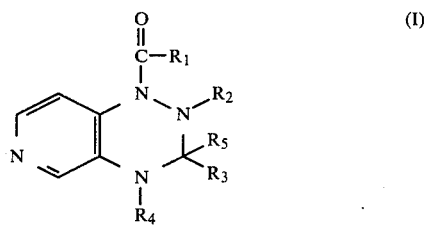

wherein $R_1$ stands for a $C_{1-20}$ alkyl group, $C_{1-4}$ alkoxy group, $C_{1-4}$ haloalkyl group, furyl group or pyridyl group or a phenyl, phenyl-($C_{1-4}$ alkyl) or phenyl-($C_{2-4}$ alkenyl) group optionally with 1 to 3 identical or different substituents on the aromatic group, said substituents being halo, trifluoromethyl, nitro, hydroxy, $C_{1-4}$ alkyl or $C_{1-4}$ alkoxy groups, $R_2$ stands for hydrogen atom or a group of the general formula $R_1$—CO—, wherein $R_1$ is as defined above, $R_3$ stands for hydrogen atom, a phenyl group having optionally a hydroxy substituent or up to 3 $C_{1-4}$ alkoxy substituents, a naphthyl group having optionally a hydroxy substituent, a phenyl-($C_{1-4}$ alkyl) group, pyridyl group or a $C_{1-20}$ alkyl group, and $R_4$ stands for hydrogen atom or a group of the general formula $R_1$—CO—, wherein $R_1$ is as defined above, and $R_5$ forms together with $R_2$ or $R_4$ a valence bond, wherein $R_2$ or $R_4$ taking part in forming said valence bond may not have the above meaning.

The scope of the invention also embraces the pharmaceutically acceptable acid addition salts of the above compounds.

The new compounds according to the invention act on the central nervous system, and can be applied primarily as antiphlogistic and analgesic agents.

Dihydropyrido[3,4-e]-as-triazine derivatives without acyl substituent are described in the Hungarian patent specifications Nos. 164,031 and 168,502. These known compounds have antimicrobial effects.

Now it has been found that when introducing one or more acyl group(s), the biological activity pattern of the pyrido[3,4-e]-as-triazine derivatives changes, and the effects on the central nervous system come into prominence. The new acylated compounds exert particularly valuable antiphlogistic effects.

In the preferred representatives of the compounds having the general formula (I)

$R_1$ stands for methyl, ethyl, n-propyl, isopropyl, capryl, stearyl, methoxy, ethoxy, chloromethyl, trifluoromethyl, benzyl, phenethyl, cinnamyl, furyl or pyridyl group, or a phenyl group optionally with one chlorine, bromine, trifluoromethyl, hydroxy or methyl substituent, $R_2$ stands for hydrogen, $R_3$ represents hydrogen or a methyl, ethyl, hexyl, octyl, nonyl, stearinyl, benzyl, phenyl, hydroxyphenyl, trimethoxyphenyl or pyridyl group, and $R_4$ stands for hydrogen or a group of the general formula $R_1$—CO—, and in this latter formula $R_1$ is as defined in the present paragraph.

Particularly preferred representatives of the new compounds according to the invention are the following derivatives:

3-phenyl-1-propionyl-1,4-dihydro-pyrido[3,4-e]-as-triazine, 3-phenyl-1-propionyl-1,4-dihydro-pyrido[3,4-e]-as-triazine hydrochloride, and 3-phenyl-1-acetyl-1,4-dihydro-pyrido[3,4-e]-as-triazine.

The pharmaceutically acceptable acid addition salts of the compounds having the general formula (I) are formed with mineral acids (such as hydrochloric acid, sulfuric acid, phosphoric acid, etc.) or organic acids (such as maleic acid, fumaric acid, citric acid, lactic acid, etc.)

The new compounds of the general formula (I) are prepared according to the invention by reacting a pyrido[3,4-e]-as-triazine of the general formula (II) or an acid addition salt thereof

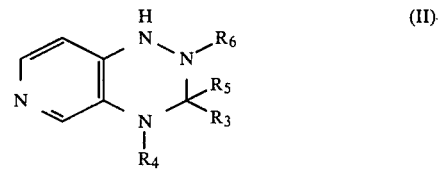

wherein $R_3$ and $R_4$ are as defined above and $R_6$ stands for hydrogen, and $R_5$ forms together with $R_6$ or $R_4$ a valence bond, with an acylating agent of the general formula (III), $$R_1-CO-X \qquad (III)$$

wherein $R_1$ is as defined above and X stands for a leaving group, preferably a halogen atom or a group of the general formula $R_1$—CO—, wherein $R_1$ is as defined above. If desired, a free base of the general formula (I) can be converted into its pharmaceutically acceptable addition salt formed with a mineral or organic acid, or, if desired, a base of the general formula (I) can be liberated from its acid addition salt.

As acylating agent of the general formula (III) one can apply either the free carboxylic acids themselves or any of their functional derivatives capable of acylating a secondary amine. Of the functional derivatives the respective acid anhydrides, acyl halides and reactive esters are preferred.

If $R_3$ stands for hydrogen, generally a 1,4-diacyl compound is obtained. If $R_3$ is other than hydrogen, generally a monoacyl derivative is obtained. An excess of the acylating agent or an inert organic solvent can be used as reaction medium.

As inert organic solvents e.g. halogenated aliphatic hydrocarbons (such as chloroform or carbon tetrachloride), aromatic hydrocarbons (such as benzene, toluene or xylene), dialkyl amides (such as dimethyl formamide), dialkyl sulfoxides (such as dimethyl sulfoxide), ethers (such as diethyl ether, dioxane or tetrahydrofuran), aliphatic hydrocarbons (such as hexane), petrol, furthermore various mixtures of the above solvents can be applied. Solvent mixtures with partially water-miscible components can be used as well.

Depending on the reactivity of the substances applied, acylation is performed generally between 10° C. and the boiling point of the solvent or solvent mixture.

When an acid is liberated in the reaction of the compounds of the general formulae (II) and (III), this acid can be bound by the reaction product, to yield directly an acid addition salt of the compound of the general formula (I). If the end-product is to be prepared in the form of a free base, acylation can be conducted in the presence of an acid binding agent. As acid binding agents inorganic or organic bases, such as alkali hydroxides (e.g. sodium or potassium hydroxide), alkali carbonates (e.g. sodium or potassium carbonate), alkali hydrocarbonates (e.g. sodium hydrocarbonate), furthermore tertiary amines, e.g. pyridine or a trialkyl amine (e.g. triethyl amine) can be applied.

The free bases of the general formula (I) can also be prepared so that the starting substance of the general formula (II) is acylated in the absence of an acid binding agent, and the resulting acid addition salt is treated with a base to liberate the required product. Examples for the bases applicable in this method are the same as listed above as acid binding agents.

If desired, the resulting free base of the general formula (I) can be converted into its acid addition salt formed with another mineral or organic acid.

The starting dihydropyrido[3,4-e]-as-triazines of the general formula (II) that contain no acyl group can be prepared as described in the Hungarian patent specifications Nos. 164,031 and 168,502.

The starting compounds of the general formula (II) that contain an acyl group can be prepared from the corresponding non-acylated derivatives by the acylation methods discussed above.

The acylating agents of the general formula (III) are either known compounds or can be prepared by known methods (Houben-Weyl, Methoden der organischen Chemie 11/2, pp. 10–14, 16–19 and 31–34).

The acute toxicity of the new compounds having the general formula (I) was tested on mice. The substances to be tested were administered orally to the animals. The $LD_{50}$ values obtained are listed in Table 1.

TABLE 1

| Toxicity | |
|---|---|
| Compound (Example No.) | $LD_{50}$ p.o. mg/kg |
| 1 | 360 |
| 11 | 500 |
| 12 (HCl) | 2000 |
| 17 | 1400 |
| 18 | 450 |
| 19 | 1500 |
| 12 | above 2000 |
| Phenylbutazone | 1000 |
| Meprobamate | 1100 |
| Amitryptiline | 225 |

The daily dose of the compounds according to invention amounts to 25 to 900 mg for adults.

The analgesic effect of the new compounds according to the invention was investigated on mice by the so-called writhing test. 0.4 ml of 0.5% acetic acid were introduced intraperitoneally into the animals, and the number of writhings was observed for a period of 5 minutes, starting from the 5th minute after challenge. The animals were treated orally with the compound to be tested one hour before the introduction of acetic acid. The animals belonging to the control group received vehicle only. The number of writhings observed for the treated group was compared to that observed with the controls, and the $ED_{50}$ values of the individual compounds (a dosage which decreases the number of writhings by 50%) was calculated from the measured data. The $ED_{50}$ values obtained in this test and the therapeutical indices ($LD_{50}/ED_{50}$) calculated therefrom are listed in Table 2.

TABLE 2

| | Analgesic effect | |
|---|---|---|
| Compound (Example No.) | $ED_{50}$ p.o. mg/kg | Therapeutical index |
| 17 | 23 | 60.87 |
| 18 | 6 | 75 |
| 19 | 75 | 20 |
| 12 | 50 | above 40 |
| Phenylbutazone | 65 | 15.4 |

The antiphlogistic effect of the new compounds according to the invention was investigated on rats by the method of Winter (J. Pharm. Exp. Ther. 141, 369/1963/). 0.1 ml of a 1% carrageenine suspension was injected subcutaneously into the plantar region of one of the hind paws. The volume of the treated paw was measured by mercuryplethysmometer before and 3 hours after challenge. The compounds to be tested were administered orally into the animals. The dosages exerting an inhibition of 30% (significant inhibiting dosage) are listed in Table 3.

TABLE 3

| | Antiphlogistic effect |
|---|---|
| Compound (Example No.) | Dosage exerting 30% inhibition mg/kg p.o. |
| 1 | 25 |
| 11 | 30 |
| 12 (HCl) | 30 |
| 18 | 12 |
| 19 | 13 |
| 12 | 26 |
| Phenylbutazone | 90 |

The effect of the new compounds exerted on the orientation reflex was tested on white mice in an eight-channel Dews apparatus, according to the method of Borsy et al. (Arch. Int. Pharmacodyn. 124, 1–2/1960/). The number of light beam interceptions, caused by the movement of the animals, was recorded after a pretreatment of 30 minutes. The test groups consisted of 3 mice. The $ED_{50}$ values obtained in the investigation of motility-inhibiting effect, furthermore the therapeutical indices ($LD_{50}/ED_{50}$) calculated therefrom are listed in Table 4.

TABLE 4

| | Motility inhibiting effect | |
|---|---|---|
| Compound (Example No.) | $ED_{50}$ p.o. mg/kg | Therapeutical index |
| 12 (HCl) | 50 | 40 |
| 17 | 30 | 46.67 |
| 19 | 90 | 16.67 |
| 12 | 35 | 57.4 |
| Meprobamate | 270 | 14.1 |

The tetrabenzine-antagonizing effect of the new compounds was tested on groups consisting of 10 mice each. The animals belonging to the control group received an oral dosage of 20 ml/kg of 0.9% aqueous sodium chloride solution, whereas the other animals were treated orally with the compound to be tested. 30 minutes after the introduction of the active agent or the vehicle 50 mg/kg of tetrabenazine (3-isobutyl-9,10-dimethyl-1,2,3,4,6,7-hexahydrobenzo[a]quinolisine-2-one) were administered orally into the animals, and the animals with closed palpebral fissures were counted 30, 60, 90 and 120 minutes after the administration of tetrabenazine. The data obtained in the individual measuring times were added, and the percentage inhibition related to the controls was calculated. The $ED_{50}$ values and the therapeutical indices ($LD_{50}/ED_{50}$) calculated therefrom are listed in Table 5.

TABLE 5

| Tetrabenazine-antagonizing effect | | |
|---|---|---|
| Compound (Example No.) | $ED_{50}$ p.o. mg/kg | Therapeutical index |
| 12 (HCl) | 40 | 50 |
| 17 | 56 | 25 |
| 19 | 20 | 75 |
| Amitryptiline | 12 | 18.75 |

The hexobarbital-induced narcosis potentiating effect of the new compounds was tested by the method of Kaergaard et al. (Arch. Int. Pharmacodyn. 2, 170/1967/) on groups consisting of 6 mice each. The animals belonging to the control group received an oral dosage of 20 ml/kg of 0.9% aqueous sodium chloride solution, whereas the other animals were treated orally with the compound to be tested. Thereafter 40 mg/kg of hexobarbital (5-/1-cyclohexenyl/-1,5-dimethylbarbituric acid) were administered intravenously into the animals. A 150% prolongation of the sleeping time, related to the average value observed in the controls, was regarded as positive response. The number of animals giving positive response was compared to the total number of the animals treated. The $ED_{50}$ values calculated from these data as well as the therapeutical indices ($LD_{50}/ED_{50}$) are listed in Table 6.

TABLE 6

| Potentiation of hexobarbital-induced narcosis | | |
|---|---|---|
| Compound (Example No.) | $ED_{50}$ p.o. mg/kg | Therapeutical index |
| 1 | 25 | 11.4 |
| 11 | 20 | 25 |
| 12 (HCl) | 10 | 200 |
| 17 | 35 | 40 |
| 19 | 150 | 10 |
| 12 | 62 | 32.3 |
| Meprobamate | 270 | 4.1 |

According to the above test results the new compounds of the general formula (I) can be applied in the therapy primarily as antiphlogistic and analgesic agents.

The invention also relates to pharmaceutical compositions containing as active agent at least one compound of the general formula (I) or a pharmaceutically acceptable acid addition salt thereof, furthermore conventional solid or liquid pharmaceutical carriers. These compositions can be prepared by methods generally known in the pharmaceutical industry.

The pharmaceutical compositions are presented preferably in the form of orally administerable preparations (such as tablets, capsules, coated tablets, solutions, suspensions, etc.) or parenterally administerable compositions (such as sterile solutions or suspensions).

The orally administerable pharmaceutical compositions may contain as additives e.g. carriers (such as gelatine, sorbite, polyvinylpyrrolidone, etc.), filling agents (such as lactose, sugar, starch, calcium phosphate, etc.), tabletting aids (such as magnesium stearate, talc, polyethylene glycol, silicium dioxide etc.), wetting agents (such as sodium lauryl sulfate) and the like.

The pharmaceutical compositions for parenteral administration may contain as additives e.g. suspending agents (such as sorbitol, sugar solution, gelatine or carboxymethyl cellulose), emulsifying agents (such as sorbitane monooleate), solvents (such as oils, oily esters, glycerol, propylene glycol or ethanol), preserving agents (such as methyl or propyl p-hydroxybenzoate) and the like.

If desired, conventional colouring and flavouring agents can also be added to the pharmaceutical compositions.

The invention is elucidated in detail by the aid of the following non-limiting Examples.

EXAMPLE 1

6.8 g (0.04 moles) of 1,4-dihydropyrido[3,4-e]-as-triazine hydrochloride are boiled in 140 ml of acetic anhydride for 4 hours, and the excess of the acid anhydride, also serving as solvent, is evaporated. 6.8 g (78.4%) of 1,4-diacetyl-1,4-dihydropyrido[3,4-e]-as-triazine are obtained; m.p.: 211°–212° C.

EXAMPLE 2

3.8 g (0.015 moles) of 3-phenyl-1,4-dihydropyrido[3,4-e]-as-triazine hydrochloride are reacted with 45 ml of chloroacetyl chloride. The reaction is started at 25° C. After one hour the mixture is heated to 85° to 90° C. and the reaction is conducted at this temperature for 10 hours. The reaction mixture is processed to obtain 4.05 g (75.2%) of 3-phenyl-1-chloroacetyl-1,4-dihydropyrido[3,4-e]-as-triazine hydrochloride, m.p.: 260°–261° C. The above process can also be carried out with 3 ml of chloroacetyl chloride, in the presence of 50 ml of benzene or chloroform.

EXAMPLE 3

3.8 g (0.015 moles) of 3-phenyl-1,4-dihydropyrido-[3,4-e]-as-triazine hydrochloride are boiled for 6 hours in 32.6 g (0.3 moles) of ethyl chloroformate. After processing the reaction mixture 4.18 g (78.6%) of 3-phenyl-1-carbethoxy-1,4-dihydropyrido[3,4-e]-as-triazine hydrochloride are obtained; m.p.: 213° C.

EXAMPLE 4

3.7 g (0.02 moles) of 3-methyl-1,4-dihydropyrido[3,4-e]-as-triazine hydrochloride are dissolved in 100 ml of trifluoroacetic acid, and the solution is maintained at room temperature for 2 hours. Thereafter 22.4 ml (0.08 moles) of trifluoroacetic acid anhydride are added to the mixture, and the reaction is conducted for additional 3 hours at 20° to 30° C. The reaction mixture is processed to obtain 5.4 g (75.5%) of 1-trifluoroacetyl-3-methyl-1,4-dihydropyrido[3,4-e]-as-triazine trifluoroacetate; m.p.: 208°–209° C.

EXAMPLE 5

3.7 g (0.02 moles) of 3-methyl-1,4-dihydropyrido[3,4-e]-as-triazine hydrochloride are reacted with an excess of caprinic acid chloride as described in Example 2, to obtain 1-caprinoyl-3-methyl-1,4-dihydropyrido[3,4-e]-as-triazine hydrochloride with a yield of 62.7%; m.p.: 237°–238° C.

EXAMPLE 6

3.8 g (0.015 moles) of 3-phenyl-1,4-dihydropyrido[3,4-e]-as-triazine hydrochloride are reacted with m-nitrobenzoyl chloride as described in Example 3 to obtain 1-(m-nitrobenzoyl)-3-phenyl-1,4-dihydropyrido[3,4-e]-as-triazine hydrochloride with a yield of 78.6%; m.p.: 206°–207° C.

EXAMPLE 7

3.7 g (0.02 moles) of 3-methyl-1,4-dihydropyrido[3,4-e]-as-triazine hydrochloride are reacted with phenylacetyl chloride as described in Example 2 to obtain 1-phenylacetyl-3-methyl-1,4-dihydropyrido[3,4-e]-as-triazine hydrochloride with a yield of 88.5%; m.p.: 273°–274° C.

EXAMPLE 8

3.8 g (0.015 moles) of 3-phenyl-1,4-dihydropyrido[3,4-e]-as-triazine hydrochloride are reacted with furan-2-carbonyl chloride as described in Example 2 to obtain 1-furoyl-3-phenyl-1,4-dihydropyrido[3,4-e]-as-triazine hydrochloride with a yield of 81.1%; m.p.: 245°–246° C.

EXAMPLE 9

3.8 g (0.015 moles) of 3-phenyl-1,4-dihydropyrido[3,4-e]-as-triazine hydrochloride are reacted with p-chlorobenzoyl chloride as described in Example 2 to obtain 1-(p-chlorobenzoyl)-3-phenyl-1,4-dihydropyrido[3,4-e]-as-triazine hydrochloride with a yield of 68%; m.p.: 215° C.

EXAMPLE 10

1.84 g (0.01 moles) of 3-methyl-1,4-dihydropyrido[3,4-e]-as-triazine hydrochloride are reacted with 10.4 g (0.05 moles) of m-trifluoromethyl-benzoyl chloride as described in Example 2. The resulting 3-methyl-1-(3'-trifluoromethylbenzoyl)-1,4-dihydropyrido[3,4-e]-as-triazine hydrochloride is treated with an aqueous solution of sodium carbonate to obtain 3-methyl-1-(3'-trifluoromethyl-benzoyl)-1,4-dihydropyrido[3,4-e]-as-triazine with a yield of 85%; m.p.: 210°–211° C.

EXAMPLE 11

3-Methyl-1,4-dihydropyrido[3,4-e]-as-triazine hydrochloride is reacted with propionic anhydride as described in Example 1, and the resulting salt is treated with an aqueous solution of potassium hydroxide. 3-Methyl-1-propionyl-1,4-dihydropyrido[3,4-e]-as-triazine is obtained with a yield of 81%; m.p.: 253°–254° C.

EXAMPLE 12

3-Phenyl-1,4-dihydropyrido[3,4-e]-as-triazine is converted into 3-phenyl-1-propionyl-1,4-dihydropyrido[3,4-e]-as-triazine as described in Example 11. The free base, melting at 208° C., is obtained with a yield of 78%. The hydrochloride of the base melts at 199°–200° C.

EXAMPLE 13

3-Octyl-1,2-dihydropyrido[3,4-e]-as-triazine hydrochloride is reacted with acetic anhydride as described in Example 1, and the resulting salt is treated with a solution of sodium hydrocarbonate to obtain 3-octyl-1-acetyl-1,2-dihydropyrido[3,4-e]-as-triazine with a yield of 75%. This compound is reacted with an equimolar amount of fumaric acid in ethanol to obtain the hydrogen fumarate melting at 285°–287° C.

EXAMPLE 14

3-Benzyl-1,2-dihydropyrido[3,4-e]-as-triazine hydrochloride is reacted with cinnamoyl chloride as described in Example 1 to obtain 3-benzyl-1-cinnamoyl-1,2-dihydropyrido[3,4-e]-as-triazine hydrochloride with a yield of 78%; m.p.: 228° C.

EXAMPLE 15

1-Furoyl-3-phenyl-1,4-dihydropyrido[3,4-e]-as-triazine hydrochloride, prepared as described in Example 8, is treated with an ethanolic solution of triethyl amine to obtain 1-furoyl-3-phenyl-1,4-dihydropyrido[3,4-e]-as-triazine with a yield of 95%; m.p.: 202°–203° C.

EXAMPLE 16

The hydrochloride obtained as described in Example 7 is treated with an isopropanol solution of dimethyl aniline to obtain 3-methyl-1-phenylacetyl-1,4-dihydropyrido[3,4-e]-as-triazine with a yield of 97%; m.p.: 183°–184° C.

EXAMPLE 17

3-Phenyl-1,4-dihydropyrido[3,4-e]-as-triazine is reacted with acetic anhydride as described in Example 11 to obtain 3-phenyl-1-acetyl-1,4-dihydropyrido[3,4-e]-as-triazine with a yield of 76%; m.p.: 208°–209° C.

EXAMPLE 18

1,4-Dihydropyrido[3,4-e]-as-triazine hydrochloride is treated as described in Example 1 to obtain 1,4-dipropioyl-1,4-dihydropyrido[3,4-e]-as-triazine with a yield of 85%; m.p.; 130°–131° C.

EXAMPLE 19

3-Phenyl-1,4-dihydropyrido[3,4-e]-as-triazine is reacted with butyryl chloride as described in Example 2 to obtain 3-phenyl-1-butyryl-1,4-dihydropyrido[3,4-e]-as-triazine with a yield of 78%; m.p.: 225°–226° C.

EXAMPLE 20

A mixture of 6 g (0.02 moles) of 1,2-dihydro-3-nonyl-pyrido[3,4-e]-as-triazine hydrochloride and 80 ml of acetic anhydride is maintained at 80° C. for 2 hours. The product separates upon cooling. 5 g (73%) of 3-nonyl-1-acetyl-1,2-dihydropyrido[3,4-e]-as-triazine hydrochloride are obtained; m.p.: 209°–210° C.

EXAMPLE 21

3-Hexyl-1,2-dihydropyrido[3,4-e]-as-triazine hydrochloride is treated as described in Example 20 to obtain 3-hexyl-1-acetyl-1,2-dihydropyrido[3,4-e]-as-triazine hydrochloride with a yield of 73%; m.p.: 215°–216° C.

EXAMPLE 22

3-(3',4',5'-Trimethoxyphenyl)-1,2-dihydropyrido[3,4-e]-as-triazine hydrochloride is treated as described in Example 20 to obtain 3-(3',4',5'-trimethoxyphenyl)-1-acetyl-1,2-dihydropyrido[3,4-e]-as-triazine hydrochloride with a yield of 85%; m.p.: 271°–272° C.

EXAMPLE 23

3.93 g (0.01 moles) of 3-stearyl-1,2-dihydropyrido[3,4-e]-as-triazine hydrochloride are reacted with stearyl chloride as described in Example 2 to obtain 1-stearoyl-3-stearinyl-1,2-dihydropyrido[3,4-e]-astriazine hydrochloride with a yield of 87%; m.p.: 79°-80° C.

EXAMPLE 24

2.75 g (0.01 moles) of 3-(p-hydroxyphenyl)-1,2-dihydropyrido[3,4-e]-as-triazine hydrochloride are reacted with pyridine-3-carbonyl chloride as described in Example 2 to obtain 1-nicotinoyl-3-(p-hydroxyphenyl)-1,2-dihydropyrido[3,4-e]-as-triazine hydrochloride with a yield of 79%; m.p.: 212°-213° C.

EXAMPLE 25

2.75 g (0.01 moles) of 3-(o-hydroxyphenyl)-1,2-dihydropyrido[3,4-e]-as-triazine hydrochloride are reacted with toluoyl chloride as described in Example 2 to obtain 1-(p-toluoyl)-3-(o-hydroxyphenyl)-1,2-dihydropyrido[3,4-e]-as-triazine hydrochloride with a yield of 73%; m.p.: 202°-203° C.

EXAMPLE 26

2.46 g (0.01 moles) of 3-(2-pyridyl)-1,2-dihydropyrido[3,4-e]-as-triazine hydrochloride are reacted with salicyloyl chloride as described in Example 2 to obtain 1-salicylol-3-(2-pyridyl)-1,2-dihydropyrido[3,4-e]-as-triazine hydrochloride with a yield of 78%; m.p.: 219°-220° C.

What we claim is:

1. An acylated pyrido[3,4-e]-as-triazine derivative of the formula (I),

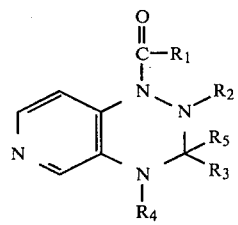

wherein
R$_1$ stands for a C$_{1-20}$ alkyl group, C$_{1-4}$ alkoxy group, C$_{1-4}$ haloalkyl group, furyl group or pyridyl group or a phenyl, phenyl-(C$_{1-4}$ alkyl) or phenyl-(C$_{2-4}$ alkenyl) group optionally with 1 to 3 identical or different substituents on the aromatic group, said substituents being halo, trifluoromethyl, nitro, hydroxy, C$_{1-4}$ alkyl or C$_{1-4}$ alkoxy groups,
R$_2$ stands for hydrogen atom or a group of the general formula R$_1$—CO—, wherein R$_1$ is as defined above,
R$_3$ stands for hydrogen atom, a phenyl group having optionally a hydroxy substituent or up to 3 C$_{1-4}$ alkoxy substituents, a naphthyl group having optionally a hydroxy substituent, a phenyl-(C$_{1-4}$ alkyl) group, pyridyl group or a C$_{1-20}$ alkyl group, and
R$_4$ stands for hydrogen atom or a group of the general formula R$_1$—CO—, wherein R$_1$ is as defined above, and R$_5$ forms together with R$_2$ or R$_4$ a valence bond, wherein R$_2$ or R$_4$ taking part in forming said valence bond may not have the above meaning, or a pharmaceutically acceptable acid addition salt thereof.

2. A compound of the formula (I) as claimed in claim 1, in which
R$_1$ stands for methyl, ethyl, n-propyl, isopropyl, capryl, stearyl, methoxy, ethoxy, chloromethyl, trifluoromethyl, benzyl, phenethyl, cinnamoyl, furyl or pyridyl group, or a phenyl group optionally with one chlorine, bromine, trifluoromethyl, hydroxy or methyl substituent,
R$_2$ stands for hydrogen,
R$_3$ represents hydrogen or a methyl, ethyl, hexyl, octyl, nonyl, stearinyl, benzyl, phenyl, hydroxyphenyl, trimethoxyphenyl or pyridyl group, and
R$_4$ stands for hydrogen or a group of the general formula —OC—R$_1$, wherein R$_1$ is as defined in claim 2, or a pharmaceutically acceptable acid addition salt thereof.

3. 3-Phenyl-1-propionyl-1,4-dihydropyrido[3,4-e]-as-triazine, 3-phenyl-1-propionyl-1,4-dihydropyrido[3,4-e]-as-triazine hydrochloride, or 3-phenyl-1-acetyl-1,4-dihydropyrido[3,4-e]-as-triazine.

4. Hydrochlorides of the compounds as defined in claim 1.

5. A pharmaceutical composition for analgesic use, containing as active ingredient an analgesically-effective amount of at least one compound of the formula (I), wherein R$_1$, R$_2$, R$_3$ and R$_4$ are as defined in claim 1, or a pharmaceutically acceptable acid addition salt thereof, and a pharmaceutically acceptable excipient.

6. A pharmaceutical composition as claimed in claim 5, in which said amount is 25 to 900 mg.

7. An antiphlogistic pharmaceutical compound containing as active ingredient an antiphlogistically-effective amount of at least one compound of the formula (I), wherein R$_1$, R$_2$, R$_3$ and R$_4$ are as defined in claim 1, or a pharmaceutically acceptable acid addition salt thereof, and a pharmaceutically acceptable excipient.

8. A composition as claimed in claim 7, wherein said amount is 25 to 900 mg.

* * * * *